(12) United States Patent
Harada

(10) Patent No.: US 9,468,358 B2
(45) Date of Patent: Oct. 18, 2016

(54) OBJECTIVE LENS FOR AN ENDOSCOPE AND ENDOSCOPE

(71) Applicant: FUJIFILM CORPORATION, Tokyo (JP)

(72) Inventor: Keisuke Harada, Saitama-ken (JP)

(73) Assignee: FUJIFILM Corporation, Tokyo (JP)

( * ) Notice: Subject to any disclaimer, the term of this patent is extended or adjusted under 35 U.S.C. 154(b) by 21 days.

(21) Appl. No.: 14/489,753

(22) Filed: Sep. 18, 2014

(65) Prior Publication Data

US 2015/0080662 A1    Mar. 19, 2015

(30) Foreign Application Priority Data

Sep. 18, 2013    (JP) ................................. 2013-192624

(51) Int. Cl.
| | |
|---|---|
| *G02B 9/08* | (2006.01) |
| *G02B 9/10* | (2006.01) |
| *A61B 1/00* | (2006.01) |
| *G02B 9/12* | (2006.01) |
| *G02B 23/24* | (2006.01) |
| *G02B 13/04* | (2006.01) |

(52) U.S. Cl.
CPC ............. *A61B 1/00096* (2013.01); *G02B 9/10* (2013.01); *G02B 9/12* (2013.01); *G02B 23/243* (2013.01); *A61B 1/00188* (2013.01); *G02B 13/04* (2013.01)

(58) Field of Classification Search
CPC ........ G02B 9/08; G02B 9/10; G02B 23/243; A61B 1/0096
See application file for complete search history.

(56) References Cited

U.S. PATENT DOCUMENTS

| | | | | |
|---|---|---|---|---|
| 5,223,982 A | * | 6/1993 | Suzuki ................. | G02B 23/243 359/708 |
| 5,812,327 A | * | 9/1998 | Doh ......................... | G02B 9/10 359/717 |
| 2003/0076584 A1 | * | 4/2003 | Nagahara ........... | G02B 13/0035 359/362 |
| 2011/0286112 A1 | | 11/2011 | Orihara | |
| 2013/0317299 A1 | * | 11/2013 | Fujii .................. | G02B 23/2438 600/176 |

FOREIGN PATENT DOCUMENTS

| | | |
|---|---|---|
| JP | 3450543 B2 | 7/2003 |
| JP | 3758801 B2 | 1/2006 |
| JP | 2009-297401 A | 12/2009 |
| JP | 4843121 B2 | 12/2011 |

\* cited by examiner

*Primary Examiner* — Darryl J Collins
(74) *Attorney, Agent, or Firm* — Young & Thompson

(57) ABSTRACT

The objective lens for an endoscope substantially consists of a first lens group having a negative refractive power, a stop, and a second lens group having a positive refractive power in this order from the object side. The first lens group consists of a single negative lens. The second lens group consists of two or fewer lenses. When the focal length of the first lens group is f1 and the focal length of the entire system is f, conditional expression (1): $-0.9 < f1/f < 0$ is satisfied.

14 Claims, 8 Drawing Sheets

EXAMPLE 1

EXAMPLE 1

EXAMPLE 2

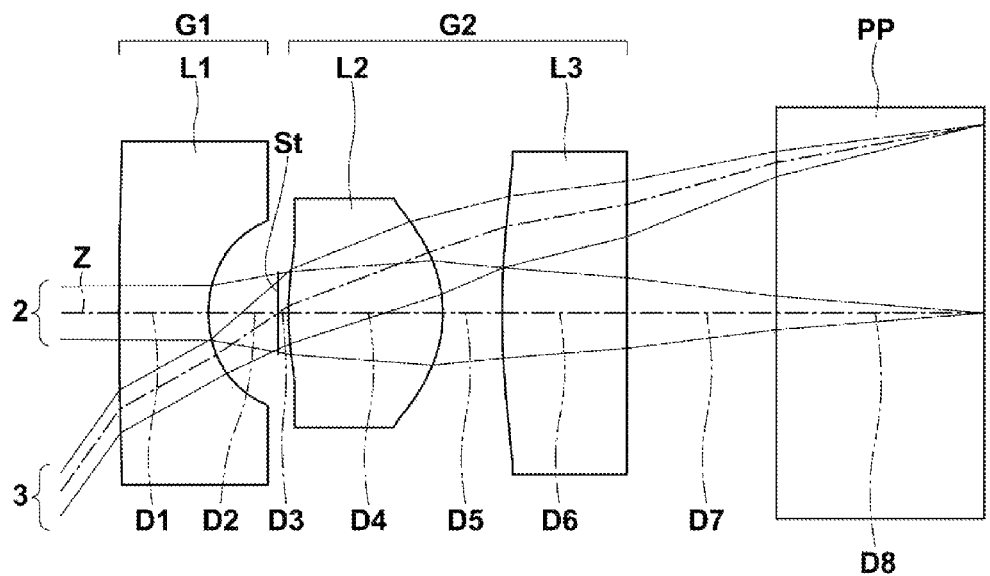
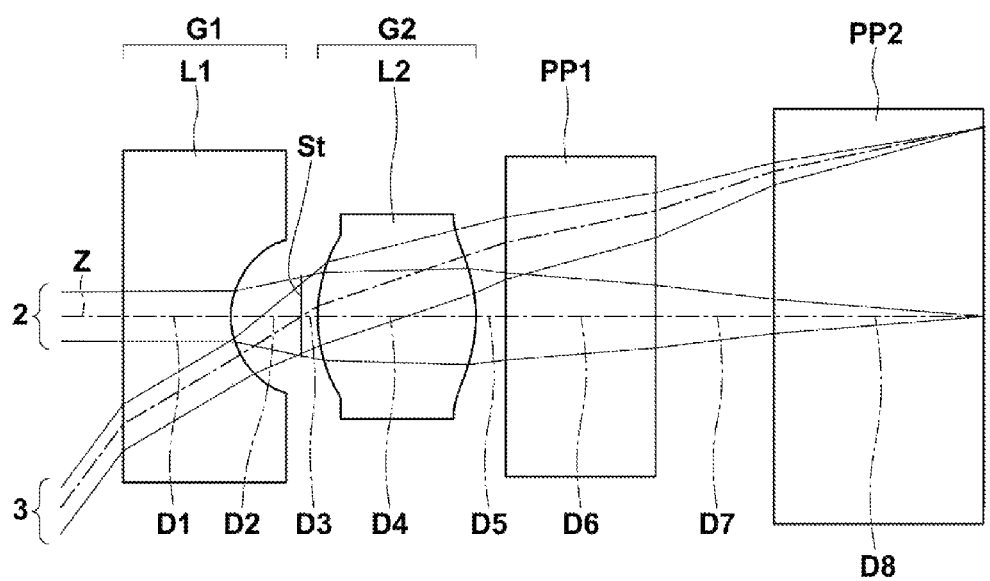

OBJECTIVE LENS FOR AN ENDOSCOPE AND ENDOSCOPE

CROSS-REFERENCE TO RELATED APPLICATIONS

The present application claims priority under 35 U.S.C. §119 to Japanese Patent Application No. 2013-192624, filed Sep. 18, 2013. The above application is hereby expressly incorporated by reference, in its entirety, into the present application.

BACKGROUND OF THE INVENTION

1. Technical Field

The present invention is related to an objective lens for an endoscope and an endoscope.

2. Description of the Related Art

Conventionally, insertion type endoscopes have been available in a medical field, for inserting an elongated insertion unit with a built-in imaging device at the tip portion thereof from the nose, mouse, etc. to pick up images of the interior of a body cavity. In addition, capsule type endoscopes also have been employed. In such capsule type endoscopes, a subject swallows a capsule that houses an imaging device and the like therein, and then the capsule picks up images of the interior of a body cavity while naturally moving through the inside of the subject. In these endoscopes, there is demand for the diameters of insertion units and the sizes of capsules to be decreased so as to reduce the burden on subjects. Accompanying these demands, objective lenses for endoscopes to be mounted on endoscopes are also being required to be miniaturized.

Miniaturized objective lenses for endoscopes have been proposed, in which the number of lenses that constitute the entire system is extremely reduced to two or three. For example, Patent Documents 1 through 4 (Japanese Unexamined Patent Publication No. 2009-297401, Japanese Patent No. 4843121, Japanese Patent No. 3758801, and Japanese Patent No. 3450543) disclose objective lenses for endoscopes constituted by a first lens group composed of a single negative lens; a stop; and a second lens group composed of one or two lenses, having a positive refractive power; in this order from the object side.

SUMMARY OF THE INVENTION

The length of a lens system in the direction of the optical axis can be shortened by reducing the number of lenses constituting the lens system. In order to decrease the diameters of the insertion section and a capsule of an endoscope, however, the length of the lens system in the radial direction should be shortened. That is, reduction of the diameter is effective. In order to reduce the diameter, there is demand for reduction of the effective diameter of rays that enter the lens disposed on the most-object side in wide angle optical systems such as objective lenses for endoscopes. Optimization of the refractive power of the most-object-side lens is significant. The objective lens for an endoscopes disclosed in Patent Documents 1 through 3, however, are not designed to mainly solve the aforementioned problems. The objective lens for an endoscope disclosed in Patent Document 4 above is a lens system in which the most-image-side surface corresponds to a planar surface that matches an image surface and the back focus is 0. Improvements are necessary for the objective lens for an endoscope disclosed in Patent Document 4 when applied for use in lens systems with finite back focus to achieve reduction of the diameters.

The present invention has been developed in view of the foregoing problems. The object of the present invention is to provide an objective lens for an endoscope having a small diameter and a favorable optical performance, and to provide an endoscope equipped with the objective lens for an endoscope.

The objective lens for an endoscope of the present invention substantially consists of a first lens group having a negative refractive power, a stop, and a second lens group having a positive refractive power in this order from the object side;

the first lens group substantially consists of a single negative lens;

the second lens group substantially consists of two or fewer lenses; and conditional expression (1) below is satisfied:

$$-0.9 < f1/f < 0 \qquad (1),\text{ where}$$

f1: the focal length of the first lens group, and
f: the focal length of the entire system.

In the objective lens for an endoscope of the present invention, it is preferable for any one of conditional expressions (1'), (2), (2'), (3), (3'), (4), (4'), (5), and (5') below to be satisfied or for arbitrary combinations thereof to be satisfied:

$$-0.85 < f1/f < 0 \qquad (1')$$

$$Nd1 > 1.55 \qquad (2)$$

$$Nd1 > 1.56 \qquad (2')$$

$$0.2 < D1/\Sigma D2i < 1.0 \qquad (3)$$

$$0.3 < D1/\Sigma D2i < 1.0 \qquad (3')$$

$$(D1/D2G) \times (Bf/|f1|) > 0.37 \qquad (4)$$

$$(D1/D2G) \times (Bf/|f1|) > 0.39 \qquad (4')$$

$$0.6 < D1St/f < 1.0 \qquad (5)$$

$$0.7 < D1St/f < 0.9 \qquad (5'),\text{ where}$$

f1: the focal length of the first lens group,
f: the focal length of the entire system,
Nd1: the refractive index with respect to the d-line of the negative lens of the first lens group,
D1: the center thickness of the negative lens of the first lens group,
$\Sigma D2i$: the sum of the center thicknesses of the lenses that constitute the second lens group,
D2G: the distance between the most-object-side lens surface of the second lens group and the most-image-side lens surface along the optical axis,
Bf: the back focus of the entire system as an air converted length, and
D1St: the distance between the object-side lens surface of the negative lens of the first lens group and the stop along the optical axis.

In the objective lens for an endoscope of the present invention, it is preferable for the negative lens of the first lens group to have the thinnest center thickness among the lenses in the entire system. Note that in the case that the objective lens for an endoscope includes a cemented lens, the center thickness refers to the center thickness of each of the lenses that constitute the cemented lens, does not refers to the center thickness of the entirety of the cemented lens.

In the objective lens for an endoscope of the present invention, it is preferable for the negative lens of the first lens group to be made of a glass material and to have at least one aspherical surface.

In the objective lens for an endoscope of the present invention, it is preferable for each of the lenses that constitute the second lens group to be made of a plastic material and to have at least one aspherical surface.

In the objective lens for an endoscope of the present invention, it is preferable for the object-side surface of the negative lens of the first lens group to be a planar surface or a convex surface.

Note that the term "substantially" in the "substantially consisting of - - - " above intends to mean that lenses substantially without any refractive power; optical elements other than lenses, such as a stop, a cover glass, and the like; lens flanges; lens barrels; and the like may be included in addition to the constituent elements listed above.

Note that the surface shapes of the above lens and the signs of the refractive powers of the above lenses and lens groups should be considered in paraxial regions if aspheric surfaces are included therein.

Note that in the present invention, a hybrid aspherical lens (an aspherical lens which is formed by laminating a film of an aspherical shape on a spherical lens) should be considered as a single lens, not as a cemented lens.

An endoscope of the present invention is equipped with the objective lens for an endoscope of the present invention described above.

The objective lens for an endoscope of the present invention is advantageous from the viewpoint of achieving a wider angle of view by adopting the retro focus type arrangement of refractive powers, and is advantageous from the viewpoint of miniaturization by setting the number of lenses of the entire system to be three or fewer. By favorably setting the configuration of a negative lens, which is disposed on the most object side, in addition to these configurations, reduction in the diameter can be achieved while maintaining favorable optical performance.

The endoscope of the present invention is equipped with the objective lens for an endoscope of the present invention. Therefore, in the case that the endoscope of the present invention is an insertion type endoscope, the diameter of the insertion unit thereof can be smaller, and in the case that the endoscope of the present invention is a capsule type endoscope, the diameter of the capsule can be reduced. In addition, excellent images can be obtained.

BRIEF DESCRIPTION OF THE DRAWINGS

FIG. 3 is a sectional diagram that illustrates the configuration of an objective lens for an endoscope of Example 3 of the present invention.

FIG. 4 is a sectional diagram that illustrates the configuration of an objective lens for an endoscope of Example 4 of the present invention.

DESCRIPTION OF THE PREFERRED EMBODIMENTS

Figure 1:
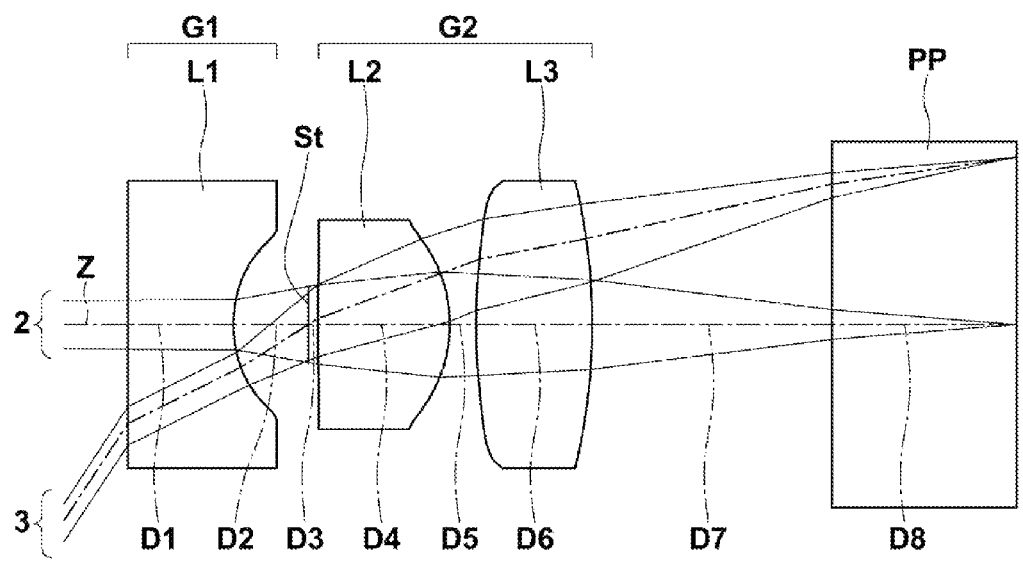
FIG. 1 is a sectional diagram that illustrates the configuration of an objective lens for an endoscope of Example 1 of the present invention.
Figure 2:
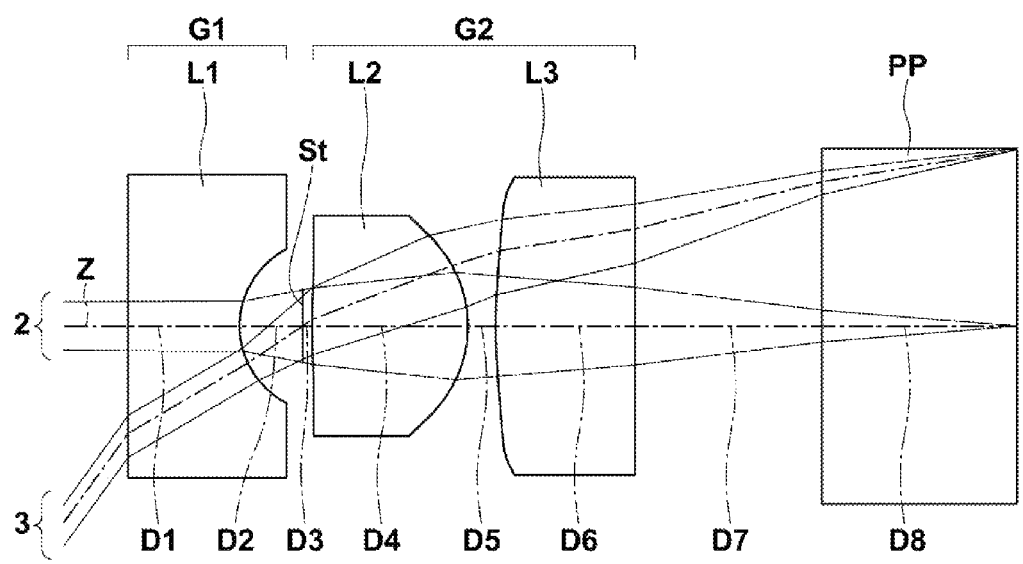
FIG. 2 is a sectional diagram that illustrates the configuration of an objective lens for an endoscope of Example 2 of the present invention.

Hereinafter, embodiments of the present invention will be described in detail with reference to the accompanying drawings. FIG. 1 is a sectional diagram of an objective lens for an endoscope according to an embodiment of the present invention, illustrating the configuration thereof with an optical axis Z. The example of the configuration shown in FIG. 1 corresponds to a lens configuration of Example 1 below. FIG. 2 through FIG. 4 show different configurations of the objective lens for an endoscope according to the embodiments of the present invention. The examples of configurations shown in FIG. 2 through FIG. 4 respectively correspond to lens configurations of Example 2 through Example 4 to be described later.

In FIG. 1, the left side is the object side and the right side is the image side. The symbol Di (i=1, 2, 3, . . . ) represents the distances between an ith surface and an i+1st surface along an optical axis Z, i being surface numbers of surfaces that sequentially increase toward the image side, with the object-side surface of the constituent element at the most-object side designated as first. FIG. 1 shows an axial light beam 2 and an off-axis light beam 3 of a maximum angle of view from an object point at the infinity distance.

The objective lens for an endoscope of the present embodiment substantially consists of a first lens group G1 having a negative refractive power, an aperture stop St, and a second lens group G2 having a positive refractive power, in this order from the object side along the optical axis Z. The first lens group G1 consists of a single negative lens. The second lens group G2 consists of less than or equal to two lenses. In the examples shown in FIG. 1 through FIG. 3, the first lens group G1 consists of a first lens L1, the second lens group G2 consists of a second lens L2 and a third lens L3 in this order from the object side. In the example shown in FIG. 4, the first lens group G1 consists of a first lens L1, and the second lens group G2 consists of a second lens L2. Note that an aperture stop St of each of FIG. 1 through FIG. 4 does not necessarily represent the shape or size thereof, but the position thereof on the optical axis.

Each of FIG. 1 through FIG. 3 shows an example in which a single plane parallel optical member PP that presumes an optical path conversion prism for bending optical paths, a filter, a cover glass, and the like is disposed on the image side of the second lens group G2. FIG. 4 shows an example in which two plane parallel optical members PP1, PP2 are disposed instead of the optical member PP in FIG. 1 through FIG. 3. However, the optical members PP, PP1, and PP2 are not the essential constituent element for the objective lens for an endoscope of the present invention. Note that in the case that the optical conversion prism is employed, bended optical paths will be formed. In FIG. 1 through FIG. 4, diagrams in which optical paths are developed are shown in order to facilitate understanding thereof. In each of the configurations of FIG. 1 through FIG. 3, the image-side surface of the optical member PP corresponds to the image surface of the objective lens for an endoscope. In the configuration shown in FIG. 4, the image side of the optical member PP2 corresponds to the image surface of the objective lens for an endoscope.

In the objective lens for an endoscope of the present embodiment, a retro focus type lens system is formed and an optical system which can favorably correspond to a wide angle of view (for example, a full angle of view of 90 or more degrees, and preferably a full angle of view of 100 or more degrees.) required for the endoscope is obtained by arranging refractive powers such that a negative lens group and a positive lens group are disposed in this order from the object side.

The distance between the aperture stop St and the most-object-side lens surface can be reduced and the maximum height of rays at the most-object-side lens surface can be lowered by forming the first lens group G1 to be of a single lens configuration. Thereby, the effective luminous flux diameter at the object-side lens surface of the first lens L1 in the first lens group G1, which is likely to become larger when widening the angle of view, can be reduced and a decrease in the diameter of the lens system can be achieved.

The distance between the aperture stop St and the most-image-side lens surface can also be reduced and the maximum height of rays at the most-image-side lens surface of the second lens group G2 can be lowered by forming the second lens group G2 disposed on the image side from the aperture stop St to include two or fewer lenses. Thereby, the effective luminous flux diameter at the most-image-side lens surface of the second lens group G2 can be reduced and a decrease in the diameter of the lens system can be achieved.

The objective lens for an endoscope of the present embodiment is configured to satisfy conditional expression (1) below:

$$-0.9 < f1/f < 0 \quad (1),\text{where}$$

f1: the focal length of the first lens group, and
f: the focal length of the entire system.

By increasing the refractive power of the first lens group G1 such that the value of f1/f is not less than or equal to the lower value defined by conditional expression (1), the maximum height of rays at the most-object-side lens surface can be lowered and the effective luminous flux diameter at the same lens surface can be reduced. Therefore, a decrease in the diameter of the lens system can be achieved. By configuring the lens system such that the value of f1/f is not greater than or equal to the upper limit defined by conditional expression (1), the first lens group G1 can have a negative refractive power, and a configuration of a retro focus type optical system can be obtained, which is advantageous from the viewpoint of achieving a wider angle of view.

It is preferable for conditional expression (1') below to be satisfied in order to set the first lens group G1 as a negative lens group and to further improve the advantageous effects related to the lower limit of conditional expression (1):

$$-0.85 < f1/f < 0 \quad (1').$$

Desirable configurations of the objective lens for an endoscope of the present embodiment will be described below. The desirable configurations described in the present specification can be arbitrarily combined and it is preferable for the configurations to be selectively adopted as appropriate, according to the items required of the objective lens for an endoscope of the present invention.

It is preferable for the objective lens for an endoscope of the present embodiments to satisfy conditional expression (2) below:

$$Nd1 > 1.55 \quad (2),\text{where}$$

Nd1: the refractive index with respect to the d-line of the negative lens of the first lens group.

By increasing the refractive index of the first lens L1 which constitutes the first lens group G1 such that the value of Nd1 is not less than or equal to the lower limit defined by conditional expression (2), the refractive power of the first lens L1 can be increased and the rays which has entered this lens can be bended more greatly. Therefore, the maximum height of rays at the first lens L1 can be lowered and the effective luminous flux diameter at the first lens L1 can be reduced. As a result, a decrease in the diameter of the lens system can be achieved. In addition, by configuring the lens system such that the value of Nd1 is not less than or equal to the lower limit defined by conditional expression (2), a wide angle of view required for the endoscope can be advantageously maintained.

It is preferable for conditional expression (2') below to be satisfied in order to further improve the advantageous effects related to conditional expression (2) above:

$$Nd1 > 1.56 \quad (2').$$

In addition, it is preferable for the objective lens for an endoscope of the present embodiment to satisfy conditional expression (3) below:

$$0.2 < D1/\Sigma D2i < 1.0 \quad (3),\text{where}$$

D1: the central thickness of the negative lens of the first lens group, and
$\Sigma D2i$: the sum of the central thicknesses of the lenses that constitute the second lens group.

$\Sigma D2i$ of conditional expression (3) corresponds to the sum of D4 and D6 in the examples of FIG. 1 through FIG. 3, and corresponds to D4 in the example of FIG. 4. By satisfying conditional expression (3), a balance between the center thickness of the lens of the first lens group G1 and the sum of the center thicknesses of the lenses in the second lens group G2 can be achieved, and both the effective luminous flux diameter at the most-object-side lens surface in the entire system and the effective luminous flux diameter at the most-image-side lens surface in the entire system can be reduced. Therefore, a decrease in the diameter of the lens system can be realized. In the case that at least either of the lower limit or the upper limit defined by conditional expression (3) is not satisfied, either of the effective luminous flux diameter at the most-object-side lens surface in the entire system or the effective luminous flux diameter at the most-image-side lens surface in the entire system will become larger. This is disadvantageous from the viewpoint of reducing the diameter of the lens system.

It is preferable for conditional expression (3') below to be satisfied in order to further improve the advantageous effects related to conditional expression (3) above:

$$0.3 < D1/\Sigma D2i < 1.0 \quad (3').$$

It is preferable for the objective lens for an endoscope of the present embodiments to satisfy conditional expression (4) below:

$$(D1/D2G) \times (Bf/|f1|) > 0.37 \quad (4),$$ where

D1: the center thickness of the negative lens of the first lens group,
D2G: the distance between the most-object-side lens surface of the second lens group and the most-image-side lens surface along the optical axis,
Bf: the back focus of the entire system as an air converted length, and
f1: the focal length of the first lens group.

Conditional expression (4) is also prepared to reduce both the effective luminous flux diameter at the most-object-side lens surface in the entire system and the effective luminous flux diameter at the most-image-side lens surface in the entire system. D2G in conditional expression (4) corresponds to the sum of D4, D5, and D6 in the examples of FIG. 1 through FIG. 3, and correspond to D4 in the example of FIG. 4. By configuring the lens system such that the value of (D1/D2G)×(Bf/|f1|) is not less than or equal to the lower limit defined by conditional expression (4), the refractive power of the first lens group G1 can be increased and the effective luminous flux diameter at the most-object-side lens surface of the first lens group G1 can be reduced.

By configuring the lens system such that the value of (D1/D2G)×(Bf/|f1|) is not less than or equal to the lower limit defined by conditional expression (4), back focus can be made longer. Therefore, the maximum height of rays at the most-image-side lens surface can be lowered and the effective luminous flux diameter at this lens surface can be reduced. As can be seen from FIG. 1 through FIG. 4, if an image height is constant, as the back focus becomes longer, the maximum height of rays at the most-image-side lens surface will become lower, and therefore the diameter of the most-image-side lens can be configured to be smaller. By configuring the lens system such that the value of (D1/D2G)×(Bf/|f1|) is not less than or equal to the lower limit defined by conditional expression (4), the outer diameter of the most-image-side lens can be smaller than the image height. For example, in the case that the objective lens for an endoscope is used in combination with an imaging element, by configuring the lens system such that the value of (D1/D2G)×(Bf/|f1|) is not less than or equal to the lower limit defined by conditional expression (4), the outer diameter of the most-image-side lens can be smaller than the length in the direction perpendicular to the optical axis at an imaging surface of the imaging element. In addition, by configuring the lens system such that the value of (D1/D2G)×(Bf/|f1|) is not less than or equal to the lower limit defined by conditional expression (4), an optical system, of which back focus is not 0 but finite unlike the optical system disclosed in Patent Document 4 described above, can be achieved; the diameter of the lens system can be reduced; a configuration, in which optical paths from the most-image-side lens to the image surface are bended, can be obtained; and a versatile optical system can be provided.

D1/D2G in conditional expression (4) is a ratio of the thickness of the first lens group G1 to the thickness of the second lens group G2 along the optical axis. By configuring the lens system such that the value of (D1/D2G)×(Bf/|f1|) is not less than or equal to the lower limit defined by conditional expression (4), back focus can be made longer and the refractive power of the first lens group G1 can be increased while suppressing the deviation of the maximum heights of rays between at the-most-object-side lens surface in the entire system and at the-most-image-side lens surface in the entire system and keeping a balance therebetween. Both the effective luminous flux diameter at the-most-object-side lens surface in the entire system and the effective luminous flux diameter at the-most-image-side lens surface in the entire system can be reduced. By satisfying conditional expression (4), a reduction in the diameter of the lens system can be achieved.

It is preferable for conditional expression (4') below to be satisfied in order to further improve the advantageous effects related to conditional expression (4) above:

$$(D1/D2G) \times (Bf/|f1|) > 0.39 \quad (4').$$

It is preferable for the objective lens for an endoscope of the present embodiment to satisfy conditional expression (5) below:

$$0.6 < D1St/f < 1.0 \quad (5),$$ where

D1St: the distance between the lens surface on the object side of the negative lens of the first lens group and the aperture stop along the optical axis, and
f: the focal distance of the entire system.

D1St in conditional expression (5) corresponds to the sum of D1 and D2 in the examples of FIG. 1 through FIG. 4. By configuring the optical system such that the value of D1St/f is not less than or equal to the lower limit defined by conditional expression (5), the center thickness of the first lens L1 within the first lens group G1 can be secured. Therefore, inclination of the first lens L1 will become less likely to occur, and favorable performance can be maintained. In addition, by configuring the lens system such that the value of D1St/f is not less than or equal to the lower limit defined by conditional expression (5), the distance between the image-side surface of the first lens L1 and the aperture stop St can be secured and correcting the field curvature satisfactorily can be facilitated while maintaining a wide angle of view. By configuring the lens system such that the value of D1St/f is not more than or equal to the upper limit defined by conditional expression (5), the effective luminous flux diameter at the object-side lens surface of the first lens L1 can be reduced and a decrease in the diameter of the lens system can be achieved. By satisfying conditional expression (5), a decrease in the diameter of the lens system can be achieved and favorable optical performance can be realized while maintaining a wide angle of view.

It is preferable for conditional expression (5') to be satisfied in order to further improve the advantageous effects related to conditional expression (5) above:

$$0.7 < D1St/f < 0.9 \quad (5').$$

In the objective lens for an endoscope of the present embodiment, it is preferable for the lens which constitutes the first lens group G1 to have the thinnest center thickness among the lenses in the entire system. Such a configuration enables reduction in the distance between the aperture stop St and the most-object-side lens surface and decrease in the diameter of the lens system. Note that in the case that the second lens group G2 consists of a cemented lens formed by cementing two lenses together, it is preferable for the center thickness of the lens that constitutes the first lens group G1 to be thinner than the center thickness of each of the lenses that constitute the cemented lens. Here, the cemented lens does not include the aforementioned hybrid aspherical lens.

In the objective lens for an endoscope of the present embodiment, it is preferable for the first lens L1 which constitutes the first lens group G1 to be made of a glass material. In such a case, a material having a high refractive index can be selected. Therefore, the refractive power of the first lens L1 can be increased and a decrease in the diameter of the lens system can be achieved. In addition, in the case that the objective lens for an endoscope is mounted on an insertion type endoscope, it is preferable for the material to have high water resistance, acid resistance, chemical resistance, and the like because the first lens L1 at the most-object side is exposed to body fluid, washing liquid, oil, and the like. Further, it is also preferable for the material to have fewer flaws and nubs thereon because the object-side surface of the first lens L1 is likely to contact with the interior of a human body. From the above, it is preferable to select a glass material.

In addition, in the case that the objective lens for an endoscope is used on the endoscope, it is preferable for the object-side surface of the first lens L1 which is located at the most-object side in the entire system to have a planar surface or a convex surface so as to prevent and reduce the occurrence of adhered matter such as fluid and the like remaining on this surface and to facilitate washing of the surface.

Further, it is preferable for the first lens L1 to have at least one aspherical surface so as to achieve favorable optical performance while configuring a small-size lens system. As described above, it is preferable for the refractive power of the first lens L1 to be increased so as to achieve miniaturization of the lens system. However, if the refractive power is made stronger, the amount of occurrence of aberrations will be likely to increase. Configuring the first lens L1 to be an aspherical lens will be advantageous from the viewpoint of satisfactory correction of aberrations. Note that in the case that the first lens L1 is a glass aspherical surface lens, it is preferable for the first lens L1 to be a glass mold lens which has high mass-productivity.

In the second lens group G2, it is preferable for each of the lenses that constitute the second lens group G2 to be made of a plastic material. In such a case, the lens system can be produced at low cost and be easily mass produced. Further, it is preferable for each of the lenses that constitute the second lens group G2 to have at least one aspherical surface so as to achieve favorable optical performance while configuring a small-size lens system.

In the examples shown in FIG. 1 through FIG. 4, each of the lenses is a single lens that has at least one aspherical surface, a first lens L1 is made of a glass material, and a second lens L2 and a third lens L3 are made of a plastic material. In the example shown in FIG. 1, the first lens L1 is a planoconcave lens with a planar surface toward the object side; and both the second lens L2 and the third lens L3 are biconvex lenses. In the example shown in FIG. 2, the first lens L1 is a planoconcave lens with a planar surface toward the object side, the second lens L2 is a biconvex lens, and the third lens L3 is a planoconvex lens with a planar surface toward the image side. In the example shown in FIG. 3, the first lens L1 is a meniscus lens with a convex surface toward the object side, the second lens L2 is a biconvex lens, and a third lens is a planoconvex lens with a planar surface toward the image side. In the example shown in FIG. 4, the first lens L1 is a planoconcave lens with a planar surface toward the object side, and the second lens L2 is a biconvex lens.

As described above, diameters can be reduced by adopting the lens configurations of the embodiment of the present invention. Specifically, for example, it will become possible to realize a lens system in which the outer diameter of a lens that is the largest among the lenses in the entire system is less than or equal to 1.5 mm, and is preferably less than or equal to 1.0 mm.

Next, Numerical Examples of the objective lens for an endoscope of the present invention will be described.

Example 1

The lens configuration of the objective lens for an endoscope of Example 1 is shown in FIG. 1. Table 1 shows the basic lens data of the objective lens for an endoscope of Example 1. In Table 1, the column of Si shows ith (i=1, 2, 3, . . . ) surface numbers that sequentially increase to the image side, with the surface at the object side of the constituent element at the most object side designated as first, the column of Ri shows the radii of curvature of ith surfaces, and the column of Di shows the distances between an ith surface and an i+1st surface along the optical axis Z. The column of Ndj shows the refractive indices of jth optical elements from the object side with respect to the d line (wavelength: 587.56 nm), and the column of vdj shows the Abbe's numbers of the jth optical element from the object side with respect to the d-line.

An aperture stop St and the optical member PP are also shown in the basic lens data. The column of the surface number of a surface corresponding to the aperture stop St indicates a surface number and the letters (St). The sign of the radius of curvature is positive in the case that a surface shape is convex on the object side, and negative in the case that the surface shape is convex on the image side.

Table 2 shows the values of specification with respect to the d-line of the objective lens for an endoscope in Example 1. In table 2, f is the focal length of the entire system, Bf is the back focus of the entire system as an air converted length, and FNo. is a F number, and $2\omega$ is a full angle of view (the unit is degrees).

In Table 1, an asterisk mark * is attached to the surface number of aspherical surfaces and the values of paraxial radii of curvature are shown in the column of the radii of curvature of the aspherical surfaces. Table 3 shows aspherical surface coefficients of these aspherical surfaces. "E-n" (n: integer) shown in the numerical values of the aspherical surface coefficients represents "$\times 10^{-n}$" in Table 3. The aspherical surface coefficient represents a value of each of coefficients KA and Am (m=3, 4, 5, . . . 16) in the aspherical surface expression below:

$$Zd = C \cdot h^2 / \{1 + (1 - KA \cdot C^2 \cdot h^2)^{1/2}\} + \Sigma Am \cdot h^m$$

where,
Zd: the depth of an aspherical surface (the length of a perpendicular line drawn from a point on an aspherical surface with a height h to a plane perpendicular to the optical axis which contacts the peak of the aspherical surface)
h: height (the distance from the optical axis to a lens surface)
C: a paraxial curvature
KA, Am: aspherical surface coefficients (m=3, 4, 5, . . . 16).

Numerical values rounded to a predetermined number of digits are shown in the following Tables. The data of the numerical values and the aberration diagrams of the objective lens for an endoscope in Example 1 are for when normalized such that the focal length of the entire system becomes 1.008.

TABLE 1

| Example 1 | | | | |
|---|---|---|---|---|
| Si | Ri | Di | Ndj | vdj |
| 1 | ∞ | 0.5242 | 1.86400 | 40.58 |
| *2 | 0.6751 | 0.3728 | | |
| 3(St) | ∞ | 0.0459 | | |
| *4 | 5.9470 | 0.6553 | 1.53112 | 55.37 |
| *5 | −0.7419 | 0.1310 | | |

TABLE 1-continued

| | | Example 1 | | |
|---|---|---|---|---|
| Si | Ri | Di | Ndj | vdj |
| *6 | 2.7243 | 0.5766 | 1.53389 | 55.96 |
| 7 | −3.1024 | 1.1899 | | |
| 8 | ∞ | 0.9174 | 1.51633 | 64.14 |
| 9 | ∞ | | | |

TABLE 2

| Example 1 | |
|---|---|
| f | 1.008 |
| Bf | 1.736 |
| FNo. | 4.00 |
| 2ω[°] | 113.6 |

TABLE 3

Example 1

| | Surface Number | | | |
|---|---|---|---|---|
| | 2 | 4 | 5 | 6 |
| KA | 1.0000000E+00 | 1.0000000E+00 | 3.1553758E−01 | 6.6843897E+00 |
| A3 | 1.2741306E−04 | 1.3281454E−02 | −1.4050063E−02 | −1.9719488E−03 |
| A4 | 2.5607857E−01 | −4.8884400E−01 | 3.3490303E−01 | −2.1505182E−01 |
| A5 | 3.2402306E−01 | 1.8864010E+00 | −1.5969946E+01 | −4.1862966E+00 |
| A6 | 3.1244436E+01 | −4.1730402E+00 | 1.3362247E+02 | 3.1601343E+01 |
| A7 | 6.0098209E+01 | 1.7797155E+01 | −5.1422760E+02 | −7.8199979E+01 |
| A8 | −4.1277419E+02 | −2.5998965E+02 | 6.3781099E+02 | −6.6395949E+01 |
| A9 | 1.3567278E+03 | 2.0997277E+03 | 1.2645963E+03 | 7.4213336E+02 |
| A10 | −1.7084266E+03 | −1.0704213E+04 | −3.6865890E+03 | −1.2538245E+03 |
| A11 | −2.7754872E+03 | 4.0364632E+04 | 9.3315829E+03 | −1.2940128E+01 |
| A12 | −1.0708297E+04 | −1.8619877E+05 | −7.1411988E+04 | 1.4740088E+03 |
| A13 | 1.7182662E+05 | 1.1106786E+06 | 2.4018221E+05 | −6.6566598E+00 |
| A14 | −6.1436374E+05 | −4.7581643E+06 | −3.5281983E+05 | −7.9482538E+02 |
| A15 | 9.7689717E+05 | 1.1032494E+07 | 2.1889075E+05 | −1.5227731E+03 |
| A16 | −6.0704449E+05 | −1.0495234E+07 | −3.6297682E+04 | 1.5991612E+03 |

Figure 5:
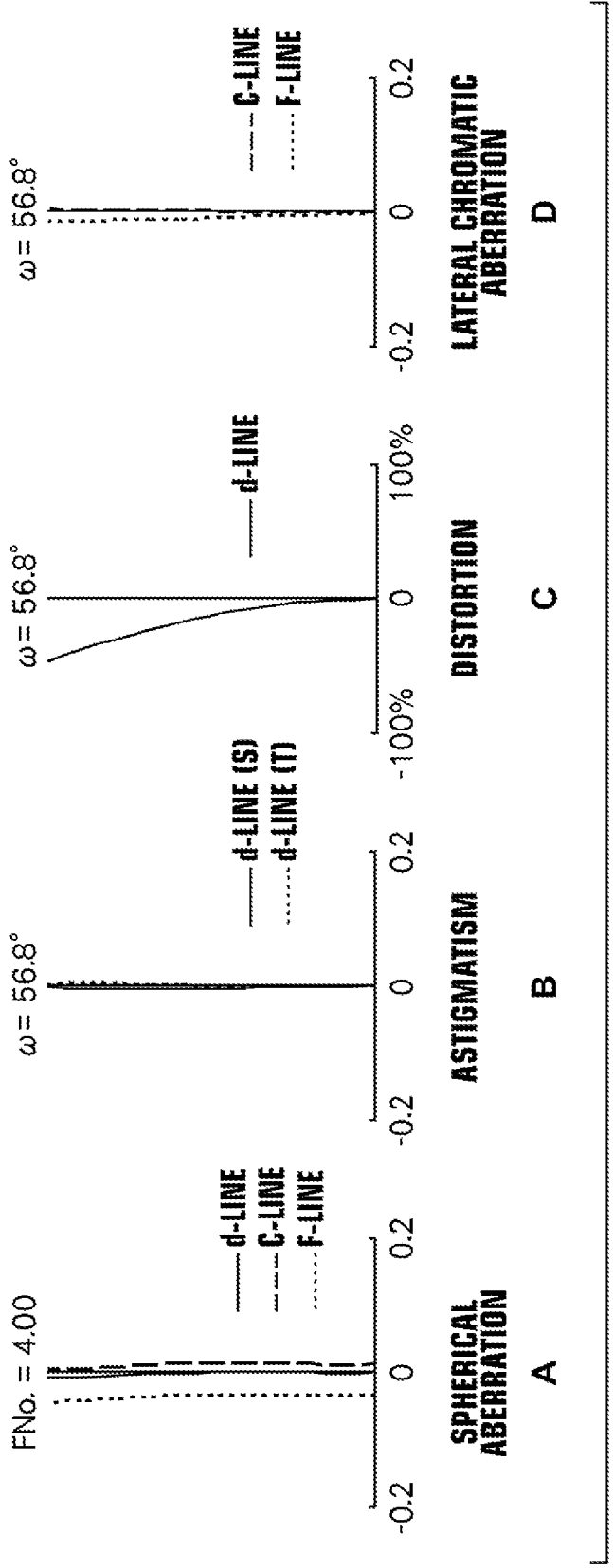
FIG. 5 is a collection of diagrams that illustrate aberrations of the objective lens for an endoscope of Example 1, wherein A illustrates spherical aberration, B illustrates astigmatism, C illustrates distortion, and D illustrates lateral chromatic aberration.

A through D of FIG. 5 respectively show spherical aberration, astigmatism, distortion, and lateral chromatic aberration of the objective lens for an endoscope in Example 1. Each of the aberration diagrams of the spherical aberration, the astigmatism, and the distortion illustrates aberration using the d-line as a standard wavelength. The diagram of the spherical aberration also shows aberration related to the C line (wavelength: 656.27 nm) and the F line (wavelengths: 486.1 nm), and the diagram of the lateral chromatic aberration shows aberration related to the F-line and the C-line. In the diagrams that illustrate astigmatism, aberrations in the sagittal direction (S) are indicated by solid lines, while aberrations in the tangential direction (T) are indicated by broken lines. In addition, "FNo." in the diagram of the spherical aberration denotes F numbers, and "ca" in the other aberration diagrams denotes half angles of view. The aberration diagrams in A through D of FIG. 5 are for when the object distance is 17.04.

The symbols in each Table, the meanings thereof, and the manners in which they are shown with respect to the aforementioned Example 1 are the same as those for the Examples below, unless otherwise noted. Accordingly, redundant descriptions thereof will be omitted.

Example 2

Figure 6:
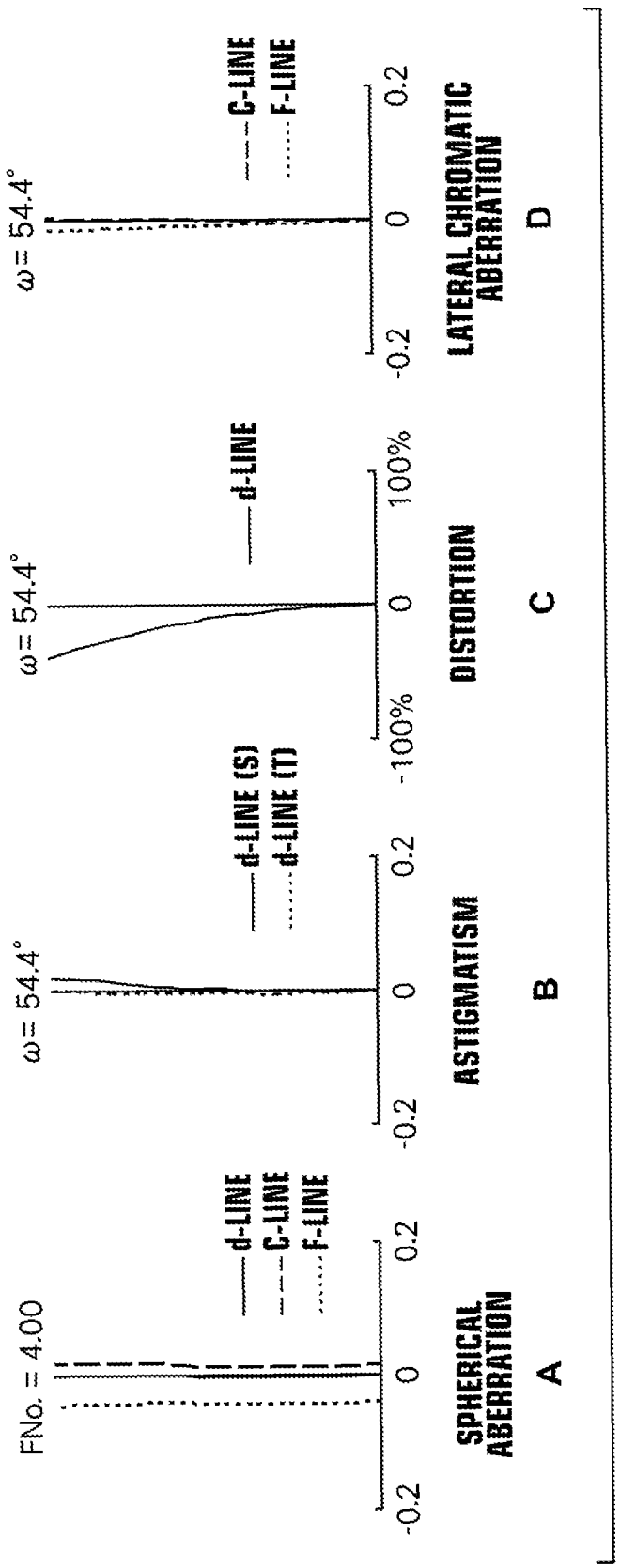
FIG. 6 is a collection of diagrams that illustrate aberrations of the objective lens for an endoscope of Example 2, wherein A illustrates spherical aberration, B illustrates astigmatism, C illustrates distortion, and D illustrates lateral chromatic aberration.

The lens configuration of the objective lens for an endoscope of Example 2 is shown in FIG. 2. Table 4, Table 5, and Table 6 respectively show basic lens data, values of specifications, and aspherical surface coefficients of the objective lens for an endoscope in Example 2. A through D of FIG. 6 respectively show aberration diagrams of the objective lens for an endoscope in Example 2. The data of the numerical values and the aberration diagrams of the objective lens for an endoscope in Example 2 are for when normalized such that the focal length of the entire system becomes 1.008. The aberration diagrams in A through D of FIG. 6 are for when the object distance is 18.03.

TABLE 4

| | | Example 2 | | |
|---|---|---|---|---|
| Si | Ri | Di | Ndj | vdj |
| 1 | ∞ | 0.5547 | 1.58913 | 61.15 |
| *2 | 0.4409 | 0.3126 | | |

TABLE 4-continued

| | | Example 2 | | |
|---|---|---|---|---|
| Si | Ri | Di | Ndj | vdj |
| 3(St) | ∞ | 0.0485 | | |
| *4 | 3.3689 | 0.7749 | 1.53389 | 55.96 |
| *5 | −0.6274 | 0.1386 | | |
| *6 | 2.9091 | 0.6933 | 1.53389 | 55.96 |
| 7 | ∞ | 0.9306 | | |
| 8 | ∞ | 0.9707 | 1.51633 | 64.14 |
| 9 | ∞ | | | |

TABLE 5

| Example 2 | |
|---|---|
| f | 1.008 |
| Bf | 1.515 |
| FNo. | 4.00 |
| 2ω[°] | 108.8 |

TABLE 6

Example 2

| | Surface Number | | | |
|---|---|---|---|---|
| | 2 | 4 | 5 | 6 |
| KA | 1.0000000E+00 | 1.0000000E+00 | 3.1553758E−01 | 6.6843897E+00 |
| A3 | −4.4736116E−07 | 1.6739695E−02 | 4.8337894E−02 | 7.0843911E−02 |
| A4 | −2.0015989E−01 | −4.9510502E−01 | −1.9834323E−01 | −8.8950319E−01 |
| A5 | 6.1322840E−03 | −1.2203066E+00 | −1.2281908E+01 | 6.1854369E−01 |
| A6 | 4.4300431E+00 | −4.5344621E−01 | 1.1820471E+02 | 1.1837837E+01 |
| A7 | 5.3752526E+00 | 7.1630144E+01 | −4.9714469E+02 | −3.4603406E+01 |
| A8 | −9.4564983E+01 | −9.6440651E+02 | 8.4096045E+02 | −1.2519098E+02 |
| A9 | 6.9699227E+02 | 5.9748108E+03 | 9.2683343E+01 | 7.8356767E+02 |
| A10 | −4.5500350E+03 | 8.3511531E+03 | −1.2880381E+03 | −1.1247861E+03 |
| A11 | 2.0997826E+04 | −4.1981326E+05 | 2.9136764E+03 | −5.9525565E+02 |
| A12 | −6.8198382E+04 | 3.1084019E+06 | −2.6156159E+04 | 2.0894369E+03 |
| A13 | 1.5258039E+05 | −1.0894258E+07 | 7.7409092E+04 | 1.6057878E+03 |
| A14 | −2.2396164E+05 | 1.6103948E+07 | −7.9652553E+04 | −6.7236365E+03 |
| A15 | 1.9439236E+05 | 4.3145419E+06 | 7.3397614E+03 | 5.6882669E+03 |
| A16 | −7.5825435E+04 | −2.8525473E+07 | 2.2463974E+04 | −1.5731282E+03 |

Example 3

Figure 7:
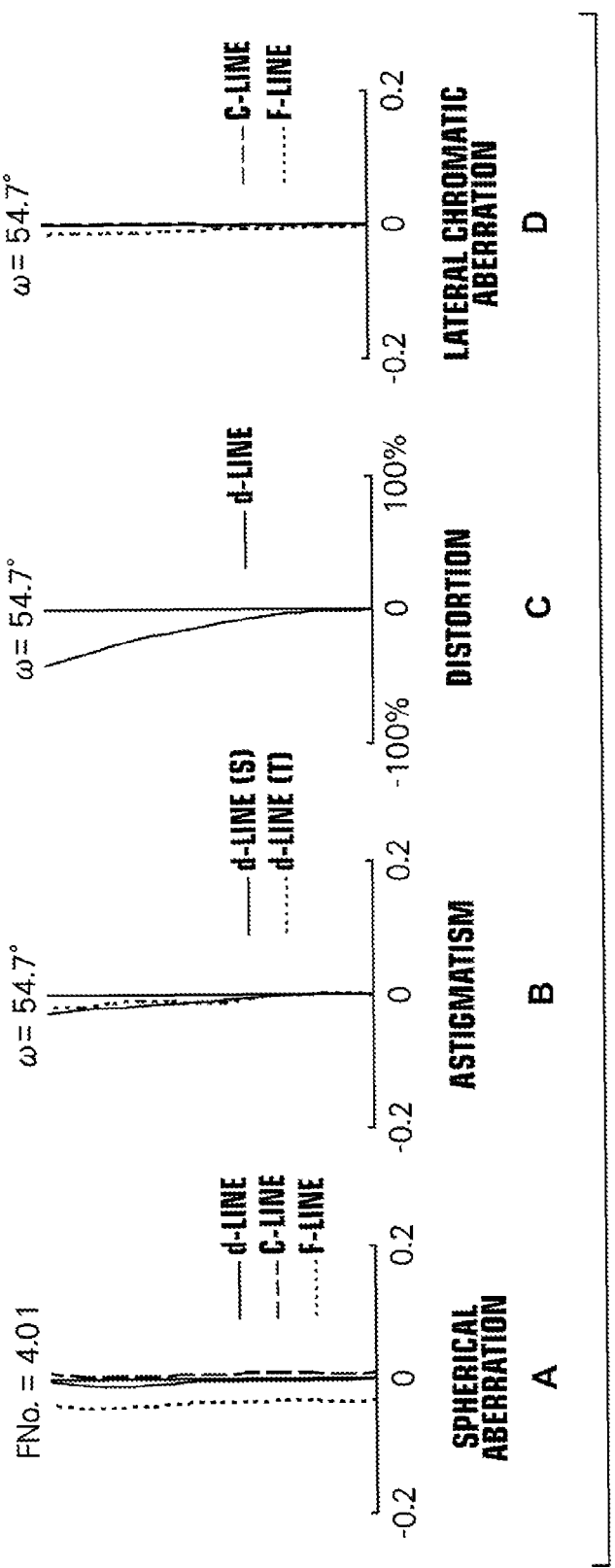
FIG. 7 is a collection of diagrams that illustrate aberrations of the objective lens for an endoscope of Example 3, wherein A illustrates spherical aberration, B illustrates astigmatism, C illustrates distortion, and D illustrates lateral chromatic aberration.

The lens configuration of the objective lens for an endoscope of Example 3 is shown in FIG. 3. Table 7, Table 8 and Table 9 respectively show basic lens data, values of specifications, and aspherical surface coefficients of the objective lens for an endoscope in Example 3. A through D of FIG. 7 respectively show aberration diagrams of the objective lens for an endoscope in Example 3. The data of the numerical values and the aberration diagrams of the objective lens for an endoscope in Example 3 are for when normalized such that the focal length of the entire system becomes 1.007. The aberration diagrams in A through D of FIG. 7 are for when the object distance is 14.84.

TABLE 7

Example 3

| Si | Ri | Di | Ndj | vdj |
|---|---|---|---|---|
| 1 | 26.7613 | 0.4012 | 1.68930 | 53.06 |
| *2 | 0.5359 | 0.3143 | | |

TABLE 7-continued

Example 3

| Si | Ri | Di | Ndj | vdj |
|---|---|---|---|---|
| 3(St) | ∞ | 0.0468 | | |
| *4 | 1.5950 | 0.6954 | 1.53389 | 55.96 |
| *5 | −0.6040 | 0.2675 | | |
| *6 | 4.8130 | 0.5617 | 1.53389 | 55.96 |
| 7 | ∞ | 0.6720 | | |
| 8 | ∞ | 0.9361 | 1.51633 | 64.14 |
| 9 | ∞ | | | |

TABLE 8

Example 3

| | |
|---|---|
| f | 1.007 |
| Bf | 1.221 |
| FNo. | 4.01 |
| 2ω[°] | 109.4 |

TABLE 9

Example 3

| | Surface Number | | | |
|---|---|---|---|---|
| | 2 | 4 | 5 | 6 |
| KA | 1.0000000E+00 | 1.0000000E+00 | 3.1553758E−01 | 6.6843897E+00 |
| A3 | −3.1961217E−05 | 3.1371977E−02 | −1.2368432E−01 | −1.2386599E−01 |
| A4 | 1.1503303E+00 | −3.3228165E−01 | 3.0322143E+00 | 1.7935775E+00 |
| A5 | −1.0655965E−01 | 7.5043741E−01 | −4.1331675E+01 | −1.0551953E+01 |
| A6 | 2.1161106E−01 | −5.0185465E−02 | 3.7144940E+02 | 2.7602711E+01 |
| A7 | −2.3103888E+01 | 1.6314402E+01 | −2.1432963E+03 | 5.0718454E+01 |
| A8 | 1.7371588E+02 | −1.7741537E+02 | 7.0813612E+03 | −6.0202414E+02 |
| A9 | −2.2967349E+02 | 2.9432503E+02 | −7.6903606E+03 | 1.7612415E+03 |
| A10 | −2.4972943E+03 | 3.3678056E+03 | −2.8185421E+04 | −2.2101481E+03 |
| A11 | 1.7509356E+04 | −7.5971787E+03 | 8.1875586E+04 | 1.3052921E+03 |
| A12 | −3.1936225E+04 | −3.1646090E+05 | 1.6906157E+05 | −3.1067129E+03 |
| A13 | −1.0746938E+05 | 3.2444467E+06 | −1.2472373E+06 | 8.5032097E+03 |
| A14 | 6.5802228E+05 | −1.4457665E+07 | 2.7007605E+06 | −7.9261937E+03 |
| A15 | −1.2818760E+06 | 3.2186210E+07 | −2.7563092E+06 | 5.4012222E+02 |
| A16 | 9.2016948E+05 | −2.9262433E+07 | 1.1287395E+06 | 1.8125138E+03 |

Example 4

Figure 8:
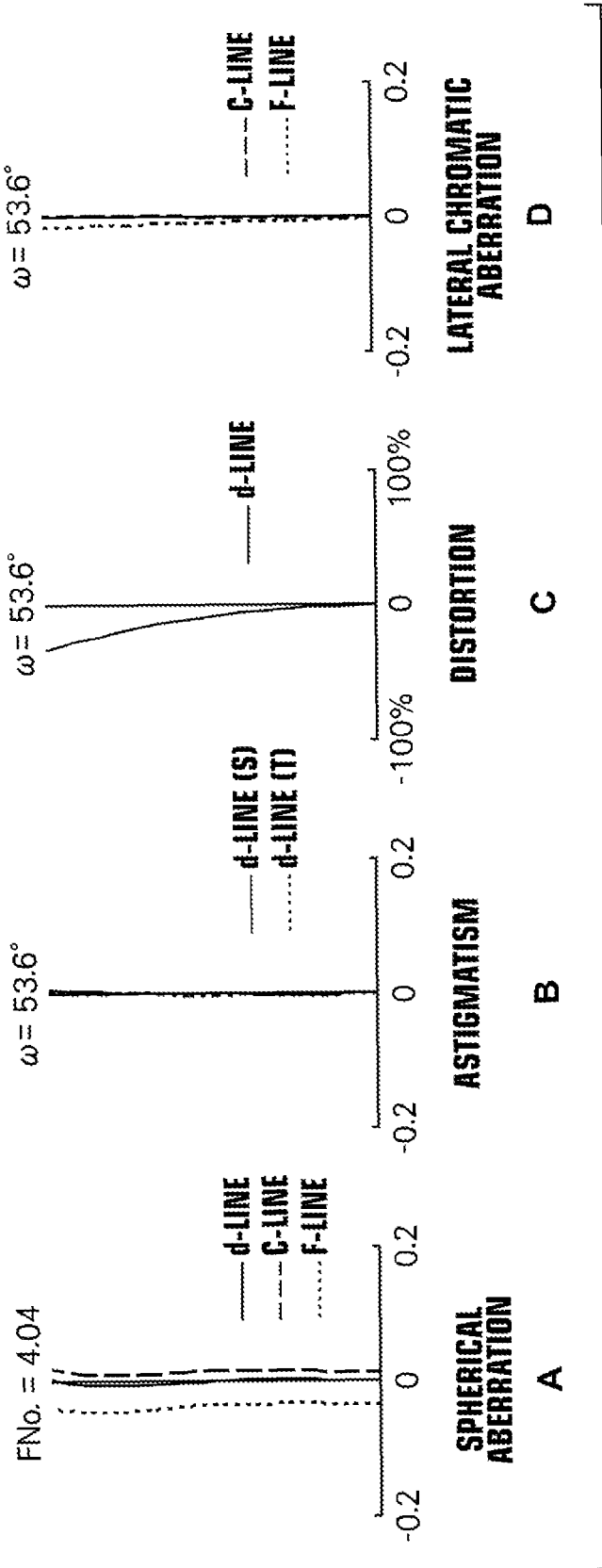
FIG. 8 is a collection of diagrams that illustrate aberrations of the objective lens for an endoscope of Example 4, wherein A illustrates spherical aberration, B illustrates astigmatism, C illustrates distortion, and D illustrates lateral chromatic aberration.

The lens configuration of the objective lens for an endoscope of Example 4 is shown in FIG. 4. Table 10, Table 11, and Table 12 respectively show basic lens data, values of specifications, and aspherical surface coefficients of the objective lens for an endoscope in Example 4. A through D of FIG. 8 respectively show aberration diagrams of the objective lens for an endoscope in Example 4. The data of the numerical values and the aberration diagrams of the objective lens for an endoscope in Example 4 are for when normalized such that the focal length of the entire system becomes 1.008. The aberration diagrams in A through D of FIG. 8 are for when the object distance is 18.81.

TABLE 10

Example 4

| Si | Ri | Di | Ndj | vdj |
|---|---|---|---|---|
| 1 | ∞ | 0.5209 | 1.56864 | 58.62 |
| *2 | 0.3892 | 0.3400 | | |
| 3(St) | ∞ | 0.0795 | | |
| *4 | 0.7839 | 0.7653 | 1.53389 | 55.96 |
| *5 | −0.7071 | 0.1447 | | |
| 6 | ∞ | 0.7235 | 1.51633 | 64.14 |
| 7 | ∞ | 0.5722 | | |
| 8 | ∞ | 1.0129 | 1.51633 | 64.14 |
| 9 | ∞ | | | |

TABLE 11

Example 4

| | |
|---|---|
| f | 1.008 |
| Bf | 1.809 |
| FNo. | 4.04 |
| 2ω[°] | 107.2 |

TABLE 12

Example 4

| | Surface Number | | |
|---|---|---|---|
| | 2 | 4 | 5 |
| KA | 1.0000000E+00 | 1.0000000E+00 | 3.1553758E−01 |
| A3 | 0.0000000E+00 | 0.0000000E+00 | 0.0000000E+00 |
| A4 | −2.8203709E−01 | −1.1222360E+00 | 7.5408886E−01 |
| A5 | −8.1315719E−03 | 3.1488933E+01 | −1.3705270E+01 |
| A6 | −3.6455468E+00 | −4.9575855E+02 | 1.9891680E+02 |
| A7 | −3.1698789E+00 | 4.7357288E+03 | −1.3696274E+03 |
| A8 | 1.2250494E+01 | −2.2028688E+04 | 4.1806024E+03 |
| A9 | −1.2273799E+02 | −1.7348543E+04 | 2.2280630E+03 |
| A10 | 2.0650617E+02 | 8.2009226E+05 | −5.2829770E+04 |
| A11 | 6.3856719E+02 | −4.4636060E+06 | 1.0873088E+05 |
| A12 | −2.5809855E+03 | 9.4871533E+06 | 1.9786760E+05 |
| A13 | −6.6479736E+03 | 5.5582718E+06 | −1.3471470E+06 |
| A14 | 5.4763754E+04 | −7.1133170E+07 | 2.7437701E+06 |
| A15 | −1.1808508E+05 | 1.3813977E+08 | −2.6764687E+06 |
| A16 | 8.9963878E+04 | −9.2344015E+07 | 1.0629520E+06 |

Table 13 shows values corresponding to conditional expressions (1) through (5) described above of the aforementioned Examples 1 through 4 and values related to each conditional expression. The data of Table 13 is related to the d-line.

TABLE 13

| Expression Number | | Example 1 | Example 2 | Example 3 | Example 4 |
|---|---|---|---|---|---|
| (1) | f1/f | −0.775 | −0.742 | −0.792 | −0.679 |
| (2) | Nd1 | 1.86400 | 1.58913 | 1.68930 | 1.56864 |
| (3) | D1/ΣD2i | 0.426 | 0.378 | 0.319 | 0.681 |
| (4) | (D1/D2G) × (Bf/|f1|) | 0.855 | 0.699 | 0.403 | 1.799 |
| (5) | D1St/f | 0.890 | 0.860 | 0.710 | 0.854 |
| | f | 1.008 | 1.008 | 1.007 | 1.008 |
| | f1 | −0.781 | −0.748 | −0.798 | −0.684 |
| | D1 | 0.524 | 0.555 | 0.401 | 0.521 |
| | ΣD2i | 1.232 | 1.468 | 1.257 | 0.765 |
| | D2G | 1.363 | 1.607 | 1.525 | 0.765 |
| | Bf | 1.736 | 1.515 | 1.221 | 1.809 |
| | D1St | 0.897 | 0.867 | 0.716 | 0.861 |

Figure 9:
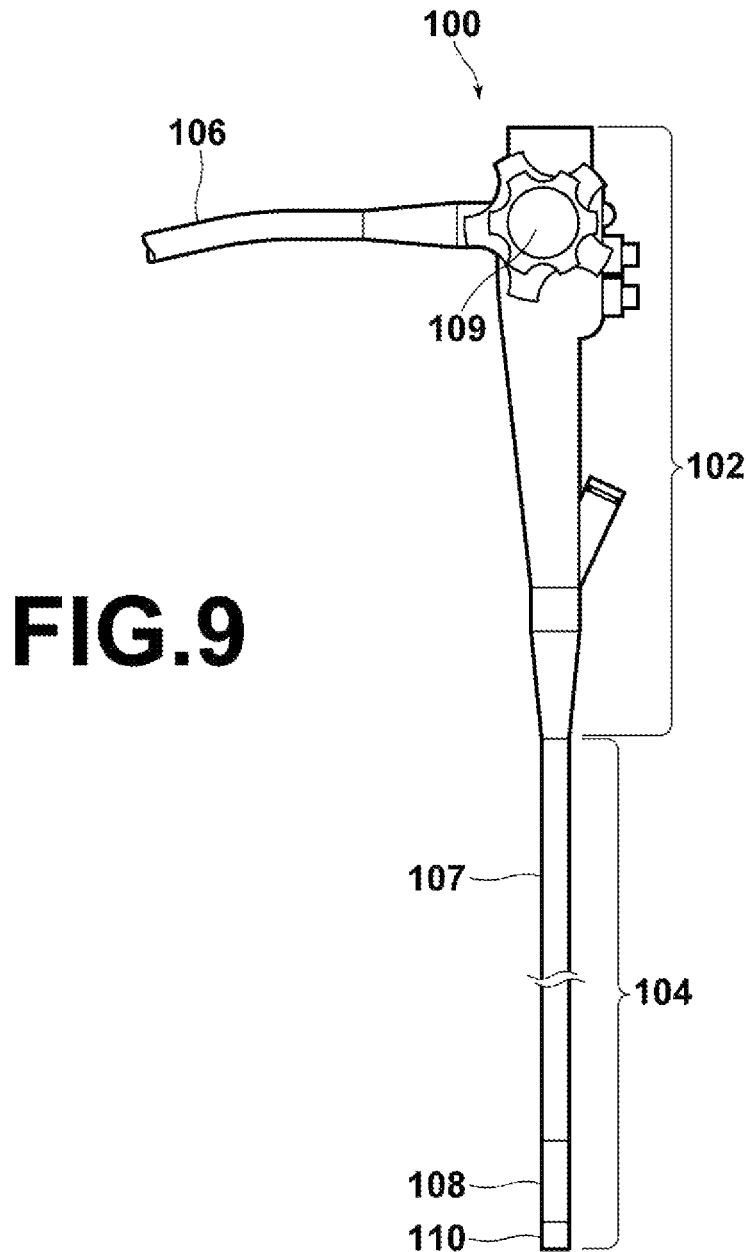
FIG. 9 is a diagram that schematically shows the configuration of an endoscope according to an embodiment of the present invention.

Next, an embodiment of an endoscope to which the objective lens for an endoscope of the present invention is applied will be described with reference to FIG. 9 and FIG. 10. FIG. 9 is a schematic diagram of the entire configuration of the endoscope. An endoscope 100 shown in FIG. 9 is mainly equipped with an operation unit 102, an insertion unit 104, and a connection unit (not shown) connected to a universal cord 106. The insertion unit 104 to be inserted into the body of a patient is connected to the distal end side of the operation unit 102, the universal cord 106 for connecting to the connection unit to be connected to a light source apparatus extends from the base end side of the operation unit 102.

A major part of the insertion unit 104 is a flexible part 107 which curves in arbitrary directions along an insertion path. A curved part 108 is connected to the tip of the flexible part 107, and the end part 110 is sequentially connected to the tip of this curved part 108. The curved part 108 is provided to direct the end part 110 toward a desired direction. The curving operation can be performed by rotating a curve operation knob 109 provided at the operation unit 102.

Figure 10:
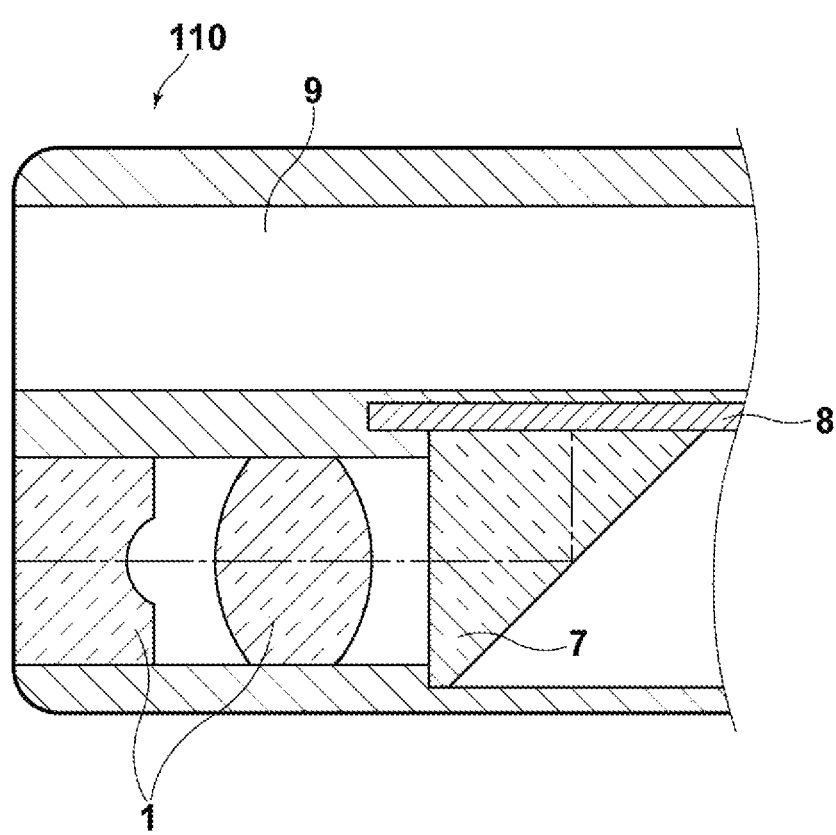
FIG. 10 is a sectional diagram of a main part of the distal end of the endoscope according to the embodiments of the present invention.

FIG. 10 shows a sectional diagram of a main part of the end part 110. As shown in FIG. 10, an objective lens for an endoscope 1, in which the optical axis thereof is disposed in parallel with a longitudinal direction of the insertion unit 104, and an optical conversion prism 7 for bending optical paths on the image side of the objective lens for an endoscope 1 by 90 degrees, and a solid state imaging element 8, which is bonded to the optical conversion prism 7 in such a manner that a light receiving surface of the solid state imaging element 8 is parallel to the longitudinal direction of the insertion unit 104, are arranged in the interior of the tip end part 110.

Note that the objective lens for an endoscope 1 is conceptually shown in FIG. 10. The solid state imaging element 8 captures an optical image formed by the objective lens for an endoscope 1 and outputs an electric signal. The solid state imaging element 8 is disposed in such a manner that an imaging surface thereof matches an image surface of the objective lens for an endoscope. Although the solid state imaging element 8 includes a cover glass for protecting the light receiving surface, the solid-state imaging element and the cover glass are illustrated as the solid-state imaging element 8 in FIG. 10. FIG. 10 shows the optical axis of the observation optical system by a dashed line. Adopting a configuration, in which the optical paths are bent as shown in FIG. 10, enables a direct viewing type observation optical system to be formed at a lower half of the tip end part 110, a treatment tool insertion channel 9 to be formed at an upper half of the tip end part 110, and a great number of elements to be placed within a small-diameter insertion unit.

The present invention was described with reference to the embodiments and Examples. The present invention is, however, not limited to the embodiments and the examples described above, and various modifications are possible. For example, values, such as the radius of curvature, the distance between surfaces, the refractive index, the Abbe number, aspherical surface coefficient of each lens, and the like are not limited to the values shown in the aforementioned Numerical Examples, but may be other values.

For example, each of the objective lenses for endoscopes of the aforementioned Examples is constituted by an aspherical surface lens. The objective lens for an endoscope of the present invention may be configured to include any of a spherical lens, a GRIN lens (gradient index lens), and a diffractive optical element or arbitrary combinations thereof.

What is claimed is:

1. An objective lens for an endoscope consisting of:
a first lens group having a negative refractive power;
a stop;
a second lens group having a positive refractive power in this order from the object side;
the first lens group consists of a single negative lens;
the second lens group consists of two or fewer lenses; and
conditional expressions (1) and (3) below are satisfied:

$$-0.9 < f1/f < 0 \qquad (1), \text{where}$$

f1: the focal length of the first lens group, and
f: the focal length of the entire system, $$0.2 < D1/\Sigma D2i < 1.0 \qquad (3), \text{where}$$

D1: the center thickness of the negative lens of the first lens group, and
$\Sigma D2i$: the sum of the center thicknesses of the lenses that constitute the second lens group.

2. The objective lens for an endoscope of claim 1, wherein conditional expression (1') is satisfied:

$$-0.85 < f1/f < 0 \qquad (1').$$

3. The objective lens for an endoscope of claim 1, wherein conditional expression (2) below is satisfied:

$$Nd1 > 1.55 \qquad (2), \text{where}$$

Nd1: the refractive index with respect to the d-line of the negative lens of the first lens group.

4. The objective lens for an endoscope of claim 3, conditional expression (2') below is satisfied:

$$Nd1 > 1.56 \qquad (2').$$

5. The objective lens for an endoscope of claim 1, wherein conditional expression (3') below is satisfied:

$$0.3 < D1/\Sigma D2i < 1.0 \qquad (3').$$

6. The objective lens for an endoscope of claim 1, conditional expression (4) below is satisfied:

$$(D1/D2G) \times (Bf/|f1|) > 0.37 \qquad (4), \text{where}$$

D1: the center thickness of the negative lens of the first lens group,

D2G: the distance between the most-object-side lens surface of the second lens group and the most-image-side lens surface along the optical axis; and
Bf: the back focus of the entire system as an air converted length.

7. The objective lens for an endoscope of claim 6, wherein conditional expression (4') is satisfied:

$$(D1/D2G) \times (Bf/|f1|) > 0.39 \qquad (4').$$

8. The objective lens for an endoscope of claim 1, wherein the negative lens of the first lens group has the thinnest center thickness among the lenses in the entire system.

9. The objective lens for an endoscope of claim 1, wherein the negative lens of the first lens group is made of a glass material and has at least one aspherical surface.

10. The objective lens for an endoscope of claim 1, wherein each of the lenses that constitute the second lens group is made of a plastic material and has at least one aspherical surface.

11. An endoscope including:
the objective lens for an endoscope of claim 1.

12. An objective lens for an endoscope consisting of:
a first lens group having a negative refractive power;
a stop;
a second lens group having a positive refractive power in this order from the object side;
the first lens group consists of a single negative lens;
the second lens group consists of two or fewer lenses; and
conditional expressions (1) and (5) below are satisfied:

$$-0.9 < f1/f < 0 \qquad (1), \text{where}$$

f1: the focal length of the first lens group, and
f: the focal length of the entire system, $$0.6 < D1St/f < 1.0 \qquad (5), \text{where}$$

D1St: the distance between the object-side lens surface of the negative lens of the first lens group and the stop along the optical axis.

13. The objective lens for an endoscope of claim 12, wherein conditional expression (5') below is satisfied:

$$0.7 < D1St/f < 0.9 \qquad (5').$$

14. An objective lens for an endoscope consisting of:
a first lens group having a negative refractive power;
a stop;
a second lens group having a positive refractive power in this order from the object side;
the first lens group consists of a single negative lens;
the second lens group consists of two or fewer lenses; and
conditional expression (1) below is satisfied:

$$-0.9 < f1/f < 0 \qquad (1), \text{where}$$

f1: the focal length of the first lens group, and
f: the focal length of the entire system,
wherein the object-side surface of the negative lens of the first lens group is a planar surface or a convex surface.

* * * * *